(12) United States Patent
Biber

(10) Patent No.: US 10,527,691 B2
(45) Date of Patent: Jan. 7, 2020

(54) LOCAL COIL ARRANGEMENT FOR USE IN AN INTERVENTION SUPPORTED BY MAGNETIC RESONANCE IMAGING

(71) Applicant: Stephan Biber, Erlangen (DE)

(72) Inventor: Stephan Biber, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 71 days.

(21) Appl. No.: 15/940,355

(22) Filed: Mar. 29, 2018

(65) Prior Publication Data

US 2018/0284202 A1    Oct. 4, 2018

(30) Foreign Application Priority Data

Apr. 4, 2017    (DE) .................. 10 2017 205 680

(51) Int. Cl.
| | | |
|---|---|---|
| *G01R 33/341* | (2006.01) | |
| *G01R 33/34* | (2006.01) | |
| *A61L 2/07* | (2006.01) | |

(52) U.S. Cl.
CPC .............. *G01R 33/341* (2013.01); *A61L 2/07* (2013.01); *G01R 33/34007* (2013.01)

(58) Field of Classification Search
CPC .............. G01R 33/341; G01R 33/3415; G01R 33/34007; G01R 33/3692; A61L 2/07; A61B 5/055; A61B 5/0042
See application file for complete search history.

(56) References Cited

U.S. PATENT DOCUMENTS

| | | | |
|---|---|---|---|
| 5,437,277 A | 8/1995 | Dumoulin et al. | |
| 5,945,827 A * | 8/1999 | Gronauer ............. | A61B 5/0555 324/318 |
| 6,157,193 A | 12/2000 | Renz et al. | |
| 2003/0016017 A1 | 1/2003 | Reykowski et al. | |
| 2004/0002648 A1 | 1/2004 | Engelhard et al. | |
| 2008/0125645 A1 | 5/2008 | Volke et al. | |
| 2009/0096456 A1 | 4/2009 | Biber et al. | |
| 2017/0276742 A1* | 9/2017 | Hengerer ............... | G01R 33/34 |

FOREIGN PATENT DOCUMENTS

| | | |
|---|---|---|
| DE | 19751017 A1 | 5/1999 |
| DE | 10130615 A1 | 1/2003 |
| DE | 10221644 A1 | 12/2003 |
| DE | 102005034838 A1 | 2/2007 |
| DE | 102007047020 B4 | 7/2012 |

OTHER PUBLICATIONS

German Office Action for German Application No. 102017205680.0, dated Dec. 1, 2017.

* cited by examiner

*Primary Examiner* — Susan S Lee

(74) *Attorney, Agent, or Firm* — Lempia Summerfield Katz LLC

(57) ABSTRACT

A local coil arrangement is provided herein. The local coil arrangement is particularly suitable for use in an intervention supported by magnetic resonance imaging. The local coil arrangement includes a plurality of electronic components such as at least one individual antenna is configured to receive a magnetic resonance signal. The local coil arrangement also includes a housing that encloses a hollow or material-filled housing interior. The electronic components are accommodated in the hermetically sealed housing interior. The housing is designed to be pressure- and temperature stable, such that the local coil arrangement is steam-sterilizable.

17 Claims, 3 Drawing Sheets

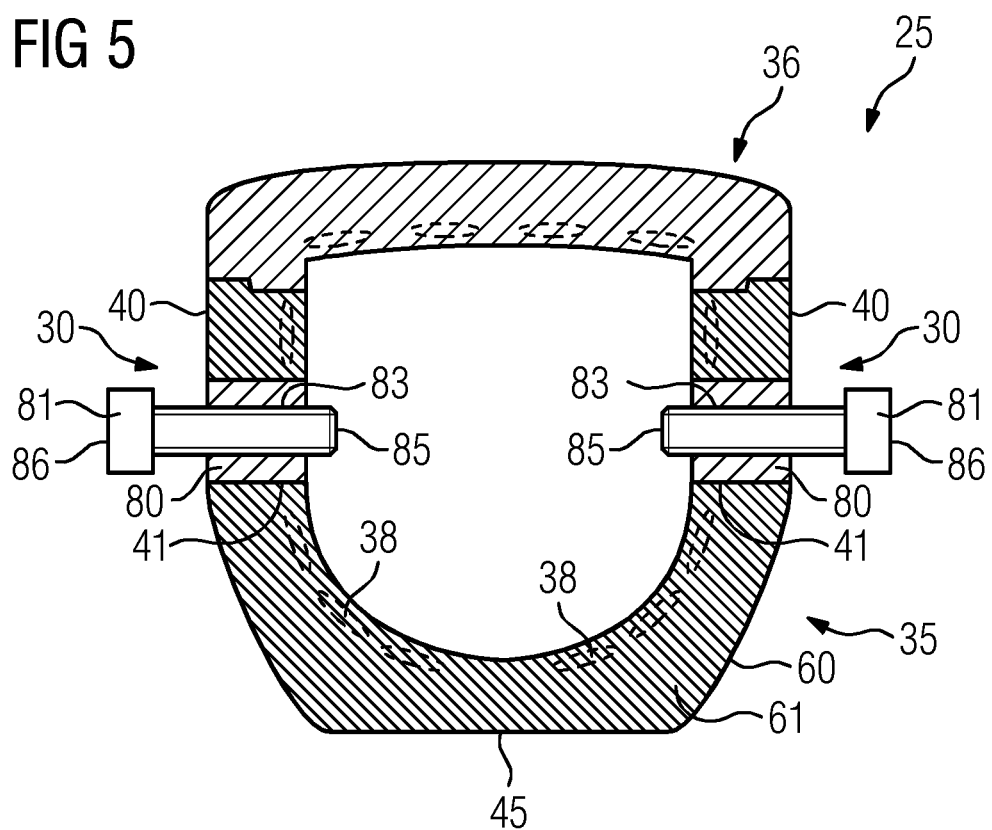

LOCAL COIL ARRANGEMENT FOR USE IN AN INTERVENTION SUPPORTED BY MAGNETIC RESONANCE IMAGING

The application claims the benefit of German Patent Application No. DE 10 2017 205 680.0, filed Apr. 4, 2017, which is hereby incorporated by reference in its entirety.

TECHNICAL FIELD

The disclosure relates to a local coil arrangement, which is provided, in particular, for use in an intervention supported by magnetic resonance imaging. The disclosure further relates to a magnetic resonance tomography (MRT) system, which includes the local coil arrangement.

BACKGROUND

Magnetic resonance tomography (MRT) is a known imaging method that may be used in medicine for diagnostic purposes, in which images are generated of the examination subject, (e.g., inside of the body of a person). To generate images, nuclear spins that are directed in a main magnetic field of the body tissue of the person to be examined are resonantly excited at a high frequency, as a result of which an electric voltage is induced in a receiving coil as a magnetic resonance signal.

Magnetic resonance imaging is increasingly used in minimally invasive interventions. For example, in a stereotaxy with real-time imaging by MRT, a medical instrument is guided to a predetermined treatment point in a patient's brain.

In order to acquire the image data for image generation with a high signal/noise ratio, the receiving coil a local coil arrangement may be used, wherein the local coil arrangement may be placed close to the body of the person to be examined in a region to be examined (e.g., close to the patient's head). The local coil arrangement may include a plurality of individual antennas (e.g., individual coils or loops), which are used to receive the magnetic resonance signal.

The use of a local coil arrangement in an operative intervention is subject to particularly high requirements in terms of hygiene, e.g., regarding the sterility of the local coil arrangement. In order to meet hygiene and cleanliness requirements, the local coil arrangement may be wrapped in a highly sterile foil (also known as a "drape"). This procedure is associated with a comparatively high cost, however. Alternatively, the local coil arrangement is arranged at a comparatively great distance from the point of intervention, which is a disadvantage in terms of image quality.

SUMMARY AND DESCRIPTION

The disclosure addresses the problem of providing a local coil arrangement that is particularly suitable for supporting an intervention by magnetic resonance imaging.

The scope of the present disclosure is defined solely by the appended claims and is not affected to any degree by the statements within this description. The present embodiments may obviate one or more of the drawbacks or limitations in the related art.

The local coil arrangement is provided for a magnetic resonance tomography system and, in particular, for use in an intervention supported by magnetic resonance imaging. The local coil arrangement includes a plurality of electronic components, such as at least one individual antenna to receive a magnetic resonance signal, and a housing, which encloses a housing interior that accommodates the electronic components. In the outward direction, the housing interior is hermetically sealed (e.g., impermeable to gases and fluids). In one example, the housing interior is hollow. In an alternative example, the housing interior is filled with material. Irrespective of these examples, the housing is designed to be pressure- and temperature-stable such that the local coil arrangement is steam-sterilizable (e.g., "autoclavable"). Here, the term steam-sterilizing (e.g., autoclaving) refers to a treatment of the housing with saturated steam at 121° C. (2 bar) to kill or inactivate microorganisms. Accordingly, the terms pressure-stable and temperature-stable may refer to the housing being subjected to a temperature of at least 121° C., and also (e.g., at the same time) may be subjected to a pressure of at least 2 bar without being destroyed.

Because the local coil arrangement is designed with a steam-sterilizable housing, it is particularly well-suited for use in interventional magnetic resonance imaging. Because the local coil arrangement itself is sterilizable, the complex workflow of wrapping the local coil arrangement in sterile foil is avoided. In addition, during the intervention, the sterile local coil arrangement may be brought particularly close to the body region that is to be monitored in the course of the intervention, as a result of which a particularly high image quality may advantageously be achieved. The high image quality in turn allows a particularly precise proximity of the medical instrument to the point in the patient's body that is to be treated, which in turn has a positive effect on the performance of the intervention.

The housing of the local coil arrangement may be made of a plastic, e.g., a polycarbonate ("PC"). Alternatively, other thermoplastics are used, such as polypropylene ("PP") or a polyamide ("PA"), and optionally also polymethyl methacrylate ("PMMA") or acryl-butadiene-styrene copolymer ("ABS").

The housing may optionally be designed to be rigid (e.g., dimensionally stable) or flexible (e.g., pliable). The flexible design of the housing advantageously allows the local coil arrangement to be applied particularly close to the examination subject, as a result of which a particularly high image quality is achieved. To manufacture a dimensionally stable housing, a polypropylene ("PP") (e.g., ethylene-propylene-diene-rubber ("EPDM")) may be used and to manufacture a flexible housing. Alternatively, the aforementioned plastics are used.

In an embodiment, the local coil arrangement is equipped to transmit the magnetic resonance signal wirelessly to a readout unit of the assigned MRT system. The wireless transmission may be achieved by inductive coupling. Optionally, a wireless energy supply is provided to the electronic components that are incorporated in the housing.

Wireless transmission may be achieved by inductive coupling because this is characterized by a particularly simple design compared with other wireless transmission techniques with regard to the electronic components needed. The inductive transmission technology is advantageously achieved by passive electronic components, which require no auxiliary energy for their operation. In particular, a frequency modulation of the MR signal or a digital encoding of the signal is advantageously not necessary and, in some examples, is also not provided. Through its comparatively simple design, the inductive coupling of the MR signal advantageously favors the sterilizability of the local coil arrangement to a particular degree.

Advantageously, through the wireless transmission, the housing may have a terminal-free design. The term "terminal-free" refers to the fact that the housing may be designed without a cable outlet (for example, for an electrical signal or supply line), and likewise is designed without an electrical terminal contact (e.g., without a plug connection) for connection to a line. In other words, the electronic components contained in the local coil arrangement do not have a galvanic connection to the outside world (e.g., allowing an exchange of electrical charges). The housing is characterized, in particular, by a surface that towards the outside is smooth (e.g., designed without grooves, ridges, splits, and suchlike) and sealed.

The fact that the housing of the local coil arrangement is designed without a plug/connection cable makes the local coil arrangement particularly highly suitable for use in a MR-assisted intervention. First, the local coil arrangement dispenses with the typically increased workload involved in the disinfection or provision of sterile cover for cables and plugs. Second, by dispensing with cables and plugs, the space required for the local coil arrangement is reduced, which conversely increases the freedom of movement of a physician providing treatment. The physician providing treatment may advantageously use the free space gained for medical instruments. In addition, the free space thus created allows improved access to the site of intervention.

In principle, the local coil arrangement may be penetrated in a conventional manner by an aperture that represents an opportunity to access a support to fix in position a part of the body that is to be treated.

The support for a part of the body may be a component of the local coil arrangement that is permanently connected to the housing. The support for a part of the body is likewise designed to be steam-sterilizable (e.g., made of a pressure- and temperature-stable material that withstands a temperature of at least 121° C. and also (e.g., at the same time) a pressure of at least 2 bar). The term "permanently connected" relates to a connection of the two components that is non-detachable or that at least cannot be detached without being destroyed. The connection point is usefully designed to be smooth (e.g., without any splits) in order to guarantee sterilizability. The support for the part of the body and the housing may be connected to each other in one piece (e.g., monolithically).

As mentioned briefly in the introduction, in a first example, the housing includes a hollow housing interior, in which the electronic components are accommodated. In an advantageous embodiment, the housing includes at least two housing components, which are assembled to form the hollow housing interior along corresponding connecting edges. To hermetically seal the housing, the corresponding connecting edges may be provided with at least one seal and joined to each other by a seamless connection. Here, a "seamless connection" is a connection in which the connecting edges are joined together by atomic or molecular forces. The seamless connection is produced in particular by gluing or welding. Additionally, or alternatively, the seamless connection, (e.g., in the case of a housing made of plastics), is produced in a plastics processing method, the connecting edges being, for example, partly fused and/or press-molded together.

Alternatively, the housing is manufactured by forming the hermetically sealed housing interior from plastics, (e.g., from a thermoplastic), and incorporating the electronic components in a molding method. Here, a "molding method" denotes a manufacturing method in which a solid body that has a defined geometric shape is manufactured from a flexible plastic. In the course of the manufacture of the housing, the electronic components are incorporated in the internal compartment thereof. In particular, the housing is manufactured in one piece. Accordingly, the housing may be designed without the aforementioned connecting edges, and as a result thereof has a particularly secure hermetic seal.

The housing may, in principle, have an at least partly hollow housing interior. The manufacture of the housing with the encapsulation of the electronic components may be provided for a housing according to the alternative example, with the housing including a material-filled housing interior, in which the electronic components are accommodated. In other words, in this case, the electronic components are embedded therein directly adjoining the material of the housing and may be entirely surrounded by the material of the housing.

Here, the housing, (e.g., and also the hollow or the material-filled, housing interior), is manufactured, in particular, in an injection molding process (e.g., the electronic components being "encapsulated" during the manufacture of the housing). The direct encapsulation of the electronic components has the advantage that there are no air-filled regions in the housing interior, in which the penetration of fluid/moisture may lead to a defect in the local coil arrangement.

In an alternative embodiment, the housing is manufactured in a foam injection molding method or from a particle foam, in which usefully, a closed-cell foam is employed. (In this case, the electronic components are "integrally foam-molded" in the manufacture of the housing.) A foam injection molding method is a conventional injection molding method in which a propellant is used, by which a foaming of the polymer melt processed in the injection molding method is triggered. To manufacture a "particle foam," pellets made of already expanded plastic are used. These expanded plastics particles ("foam particles") are sintered under the effects of heat and pressure to form a coherent solid, in which the foam structure of the pellets remains preserved. This integral foam-molding results in the housing having a material- and weight-saving design compared with a solid piece made of plastic. In addition, the integral foam-molding of the electronic components has the advantage that a particularly low-pressure load is exerted on the electronic components. As a result, in the housing manufacturing process, damage to the electronic components is effectively avoided.

In a further embodiment, in the housing interior that accommodates the electronic components, a moisture sensor and/or a temperature sensor is/are arranged. The moisture sensor is provided in order to check whether moisture that may damage the local coil arrangement has entered the housing interior during an autoclaving process. The temperature sensor is provided in order to check whether the local coil arrangement has been exposed to a damaging excessive temperature during an autoclaving process which may damage the functional efficiency of the electronics or the functionality of the housing.

In one embodiment, the housing is manufactured from a transparent material in at least one section, such that a visual inspection of the housing interior may be carried out. This embodiment proves to be useful in particular for a housing with a hollow housing interior. The at least partly transparent housing allows an optical checking of the electronic components in a simple manner. Nevertheless, in certain embodiments, the housing may be at least partly manufactured from a transparent material, and a moisture sensor and/or a temperature sensor may be arranged in the housing interior. As a result, it is possible and also intended for the moisture sensor and/or the temperature sensor to be able to be optically evaluated through the transparent housing component. In an embodiment that is particularly simple to achieve, an indicator testing strip is used as both a moisture sensor and/or as a temperature sensor, wherein, for example, exceeding a specified critical moisture content or exceeding a specified critical temperature brings about a specific color change in the testing strip. Such indicator testing strips may be based on a chemical or biological process (involving, for example, bacteria, which act as indicators of moisture or of the presence of other impurities).

The local coil arrangement may be designed as a head coil array (also known for short as a "head coil"), which is equipped to be applied to a patient's head. Other design variants (for example, as a knee coil array) are also possible.

The magnetic resonance tomography system includes a local coil arrangement according to the description in the aforementioned.

The local coil arrangement may be equipped to transmit the magnetic resonance signal wirelessly to a readout unit of the assigned MRT system, the housing being designed to be terminal-free. Accordingly, in this embodiment, the MRT system includes a readout unit equipped to receive the MR signals that have been transmitted wirelessly by the local coil arrangement, and a computation unit connected by signal technology to the readout unit, which is equipped to evaluate the MR signals received.

For example, the local coil arrangement includes a plurality of individual antennas, the readout unit including a plurality of readout antennas, and the individual antennas of the local coil arrangement being magnetically (e.g., inductively) coupled with the readout antennas of the readout unit. Here, the transmission of the MR signals is achieved in particular as disclosed in German Patent Application No. DE 10 2007 047 020 B4. The inductive coupling, together with the design of the local coil arrangement described in the aforementioned, leads to a particularly high robustness of the local coil arrangement, making it able to withstand autoclave treatment.

For identifying a (e.g., wireless) local coil arrangement, the computation unit may be equipped to detect the presence of the local coil arrangement based on the presence of a connector (not connected) that is separate from the local coil arrangement at a specified port in the MRT system. The port is usefully located in a region of the MRT system that is uncritical with regard to the space required for the intervention. The identification of the local coil arrangement optionally ensues by a software-based user query.

BRIEF DESCRIPTION OF THE DRAWINGS

Exemplary embodiments of the disclosure are explained below with reference to the drawings, in which:

FIG. 5 depicts an alternative embodiment of the head coil as illustrated in FIG. 3.

Components and values that are identical to one another are denoted by the same reference signs in all the figures.

DETAILED DESCRIPTION

Figure 1:
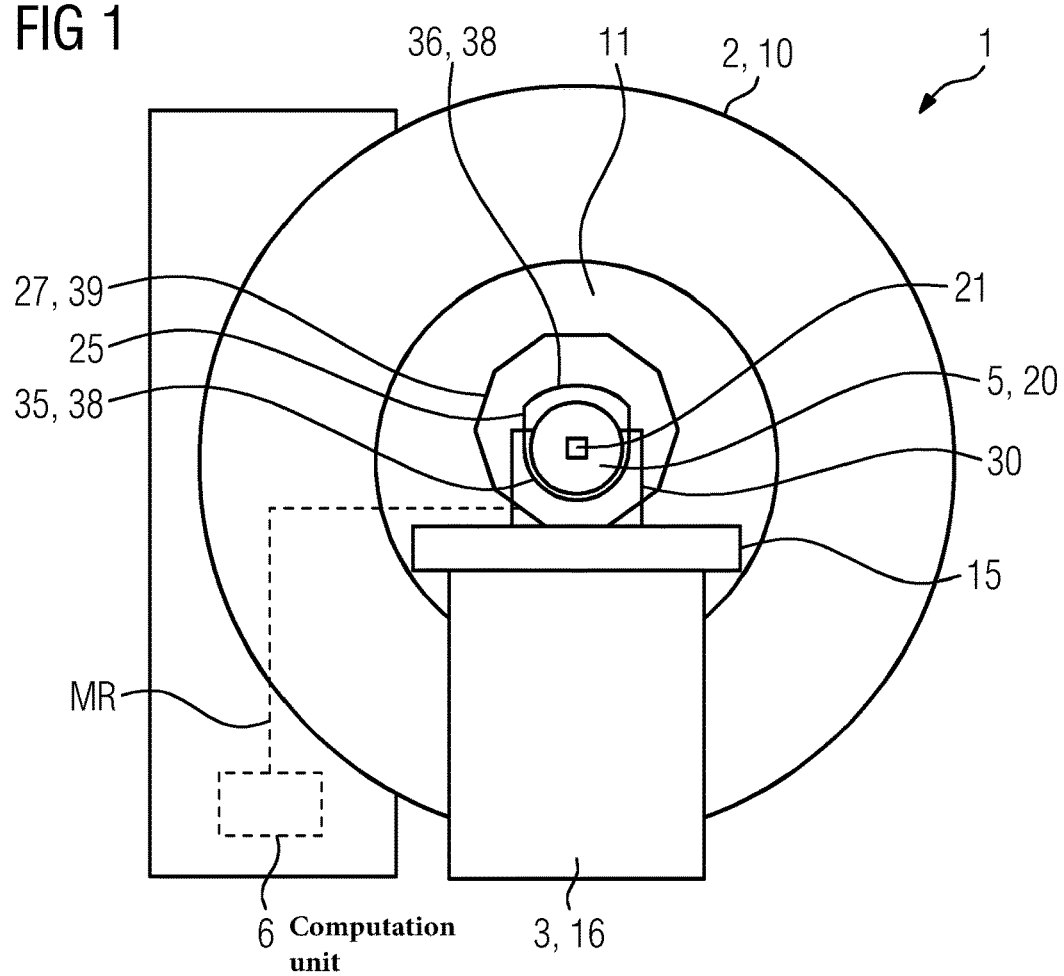
FIG. 1 depicts a schematic representation of an example of a MRT system to support an intervention on a patient's head, in which the MRT system includes a head coil and also a head support.

FIG. 1 depicts a schematic representation of a magnetic resonance tomography (MRT) system 1, with a magnetic resonance tomograph (MRT) device 2 for MRT imaging. A patient table 3 to accommodate a person who is to be examined or treated (referred to below as "patient 5") is assigned to the MRT device 2. The MRT system 1 further includes a computation unit 6, which is used to activate the MRT device 2 and the patient table 3, and to display a magnetic resonance image on a display unit.

The MRT device 2 is conventional in design. It includes main magnetic coils to generate a main magnetic field, high frequency coils to resonantly excite nuclear spins in the body tissue of the patient 5, and a gradient coil system for spatial resolution of a magnetic resonance (MR) signal MR resulting from the resonant excitation. The aforementioned coil system of the MRT device 2 is accommodated in an MRT housing 10, through which runs a tunnel 11. Inside the tunnel 11 (in the interior thereof), an image acquisition zone of the MRT device 2 is defined, in which the MRT imaging is achieved.

The patient table 3 includes a patient couch 15, which may be moved translationally in relation to a fixed foot 16 of the patient table 3 along the axis of the tunnel 11 at least partly into or out of said tunnel.

The MRT system 1 is used for imaging support for an intervention on the patient 5, with an intervention on the head 20 of the patient 5 being indicated here by way of example. In the intervention, a guide 21 (also known as a "Smart-Frame") attached to the head 20 to guide a medical instrument is used, for example. Because the disclosure does not relate to the intervention itself, the guide 21 is only indicated symbolically.

The MRT system 1 further includes a head coil 25 and a readout unit 27. The head coil 25 frames the head 20 of the patient 5, with an axis A (see FIG. 2) of the head coil 25 being oriented approximately along the body axis of the patient 5. Because the head coil is close to the body, the head coil 25 receives the MR signals MR with an improved signal-noise ratio compared with the aforementioned coil system. The head coil 25 transmits the MR signals MR that have been received wirelessly to the readout unit 27, which encases the head coil 25 coaxially at a distance. The readout unit 27 for its part is connected to the computation unit 6 in order to forward the MR signals MR.

Finally, the MRT system includes a head support 30, indicated schematically, which in the exemplary embodiment shown is configured in a conventional design. The head support 30 is used to fix the head 20 in its position (e.g., during the intervention).

In the exemplary embodiment shown, the head coil 25 includes a first local coil arrangement 35, which encircles the back of the patient's head according to the intended use thereof, and also a second local coil arrangement 36, which is turned towards the face of the patient 5, according to the intended use thereof. The two-part design of the head coil 25 makes it easier to fit it to the head 20 of the patient 5.

Each of the local coil arrangements 35, 36 respectively includes a plurality of individual antennas 38, (e.g., designed as coils), and which are arranged in what is known as a "Loop Array". Second, the readout unit 27 likewise includes a plurality of readout antennas 39, which are wirelessly connected to the individual antennas 38 of the respective local coil arrangement 35, 36 by a magnetic or an inductive coupling when in operation. Signal transmission between the individual antennas 38 and the readout antennas 39 is achieved in particular as described in German Patent Application No. DE 10 2007 047 020 B4.

In an alternative embodiment, it is also conceivable for the signal transmission from the local coil arrangements 35, 36 (or from the individual antennas thereof 38) to the readout unit 27 to be achieved by radio or by optical data transmission.

Signal transmission from the readout unit 27 to the computation unit 6 is achieved in this case by a cable connection. Due to the wireless signal transmission from the local coil arrangements 35, 36 to the readout unit 27, no signal cable is necessary on the respective local coil arrangement 35, 36. Each local coil arrangement 35, 36 is designed accordingly without an outgoing cable and also without a connector to connect the local coil arrangement to a cable. Due to the cable-free design of the local coil arrangements 35, 36, the physician conducting the intervention advantageously has a particularly large amount of space available to move around in.

Departing from the representation, it is alternatively also possible for the readout unit 27 to be designed in a flat cuboid shape, wherein the readout unit 27 is arranged between the head coil 25 and the patient couch 15 such that the free space for the operating physician is enlarged considerably. The readout unit 27 is optionally incorporated into the patient couch 15.

For identifying the wireless local coil arrangements 35, 36, a port is provided on the MRT system 1 for a connector that is separate from the local coil arrangement 35, 36. The port is arranged in a region that is not critical for the intervention. If the connector that is separate from the local coil arrangement 35, 36 is plugged into this port, the computation unit 6 concludes from the fact that the port is occupied that the assigned local coil arrangement 35, 36 is connected to the MRT system. The identification of the local coil arrangement 35, 36 is optionally software-based, a plurality of inductive coil arrangements being offered to a user to select from, such that the user may select the local coil arrangement 35, 36 that is actually connected. In this case, the identification of the local coil arrangement 35, 36 does not ensue automatically through the MRT system 1, but through the relevant user input.

Figure 2:
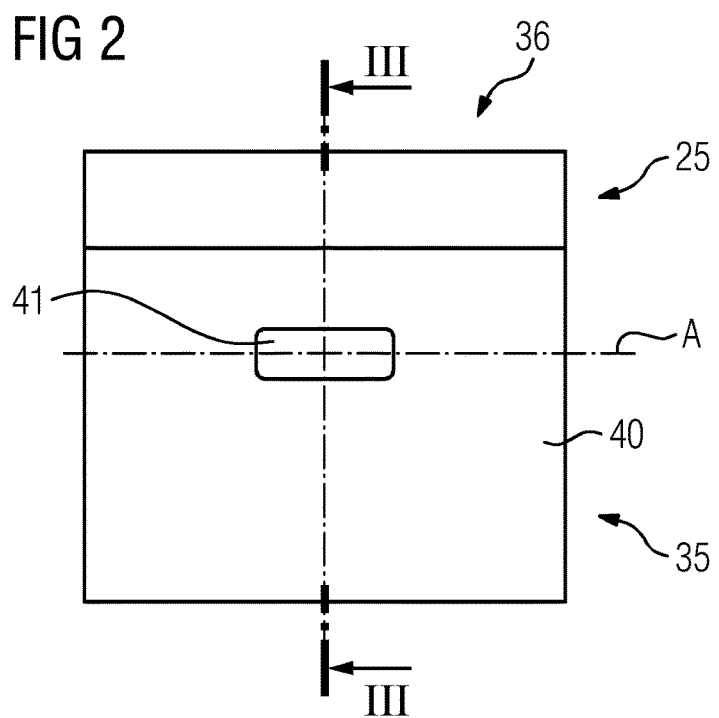
FIG. 2 depicts an individual schematic representation of a side view of the head coil according to FIG. 1.

FIG. 2 depicts the head coil 25 in a schematic side view—in particular not shown to scale. It may be seen from FIG. 2 that the first local coil arrangement 35 (e.g., assigned to the back of the head) has a continuous aperture 41 in a side wall 40 that flanks the head of the patient 5 according to its intended use. The aperture 41 is used to access the head support 30. A corresponding aperture 41, which is not shown, is also incorporated in the side wall 40.

Optionally, the walls of the head coil 25 are penetrated by further apertures in order to increase patient comfort and provide better access to the patient.

It may additionally be seen from FIG. 2 that the head coil 25 as a whole, and hence the two local coil arrangements 35, 36 too, are designed without a connection cable and without a plug to connect to a cable. Both local coil arrangements 35, 36 are designed towards the outside with a smooth surface, "smooth" denoting a surface without grooves/ridges/splits and suchlike).

Figure 3:
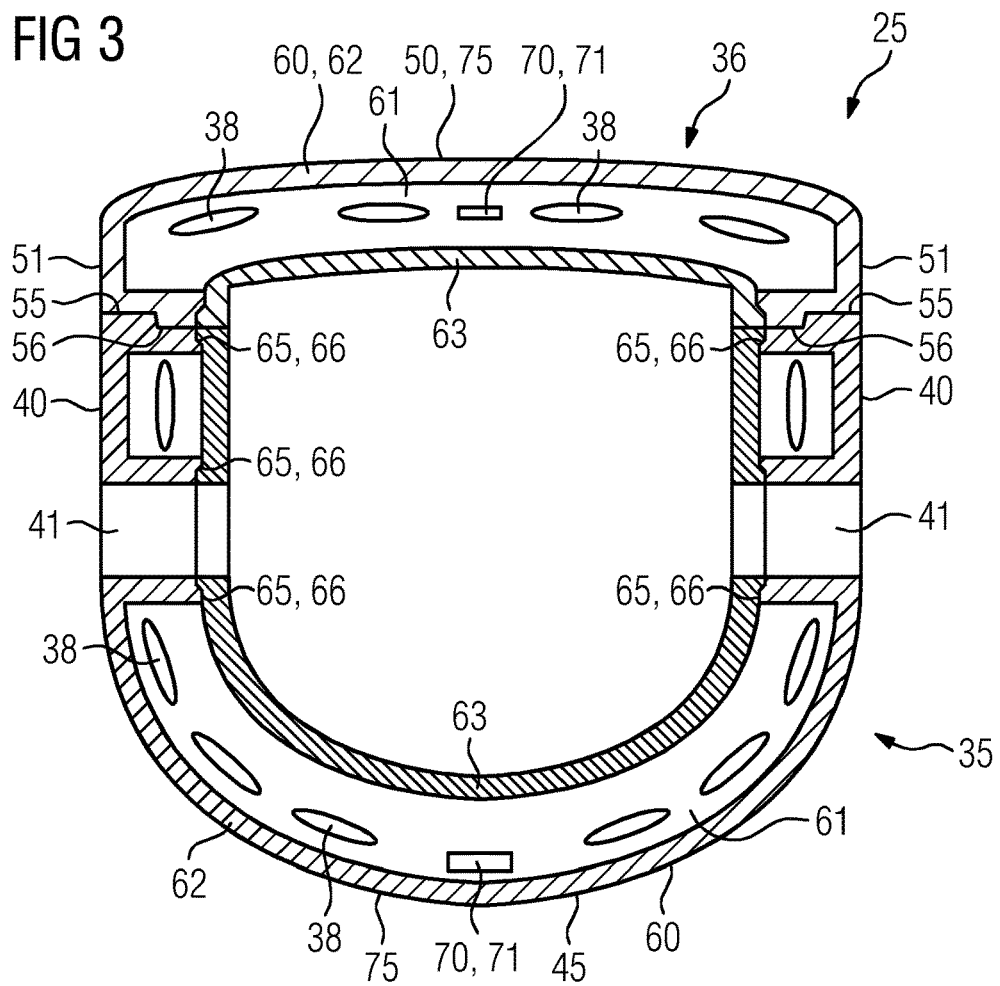
FIG. 3 depicts a schematic representation of a III-III cross section through the head coil according to FIG. 2.

FIG. 3 depicts the head coil 25 in a cross section. The first local coil arrangement 35 is seen in cross section in an approximately "U-shaped" design, with the side walls 40 that flank the back of the head of the patient 5 protruding above a curved rear wall 45 on both sides. The second local coil arrangement 36 is likewise roughly U-shaped in design, with however, the rear wall thereof 50 scarcely being curved, and the side walls thereof 51 having a clearly lower height compared with the side walls 40.

It may be further seen from the cross-sectional representation in FIG. 3 that the first local coil arrangement 35 and the second local coil arrangement 36 are placed one over the other along their front faces 55, 56 at the free end of the respective side walls 40, 51. Along the front faces 55, 56, steps are formed that are in each case designed to complement each other, such that the two local coil arrangements 35, 36 are fixed in their relative position with regard to each other. In the connected state, the two local coil arrangements 35, 36 complete each other to form the roughly ring-shaped head coil 25.

Each of the two local coil arrangements 35, 36 includes in each case a housing 60, which in the embodiment shown in FIG. 3 encloses in each case a hollow housing interior 61.

Each housing 60 includes in each case a housing shell 62 and also a housing cover 63 that seals the shell 62, which are manufactured in each case as molded plastics components, made of polypropylene (PP) for example. As a result, the housing 60 is pressure- and temperature-stable.

Each housing shell 62 and each housing cover 63 are assembled together at corresponding connecting edges 65, 66. The connecting edges 65, 66 are designed in each case with a step that is complementary to the corresponding connecting edge 65, 66, such that in each case an abutment is formed for the housing cover 63 that is placed on top. To produce a gas- and moisture-impermeable seal for the housing interior, the connecting edges 65, 66 that meet together are in each case (e.g., plastic-) welded.

Alternatively, the connecting edges 65, 66 that meet together are hermetically sealed with the aid of a (e.g., heat-resistant) seal. Alternatively again, the connecting edges 65, 66 are glued together.

A plurality of electronic components is accommodated in the housing interior 61, that is, in each case, the individual antennas 38 (indicated schematically as ellipses), and also further electronic components (for example, condensers, tuning circuits with diodes), which are not shown in further detail. Furthermore, in each housing interior 61, a (e.g., moisture) sensor 70, and also a (e.g., temperature) sensor 71 are accommodated in each case. The sensors 70, 71 are each designed here as indicator test strips, which signal by a color change when a specified moisture content or a specified temperature has been exceeded. So that the sensors may be read, each housing 60, (to be precise, each housing shell 62), is manufactured from transparent plastic in a section 75 that surrounds the sensors 70, 71.

Due to the hermetic encapsulation of the electronic components, each local coil arrangement 35, 36 is suitable for steam sterilization, such that after autoclaving, it may be used for the intervention shown in FIG. 1 without taking any further measures.

Figure 4:
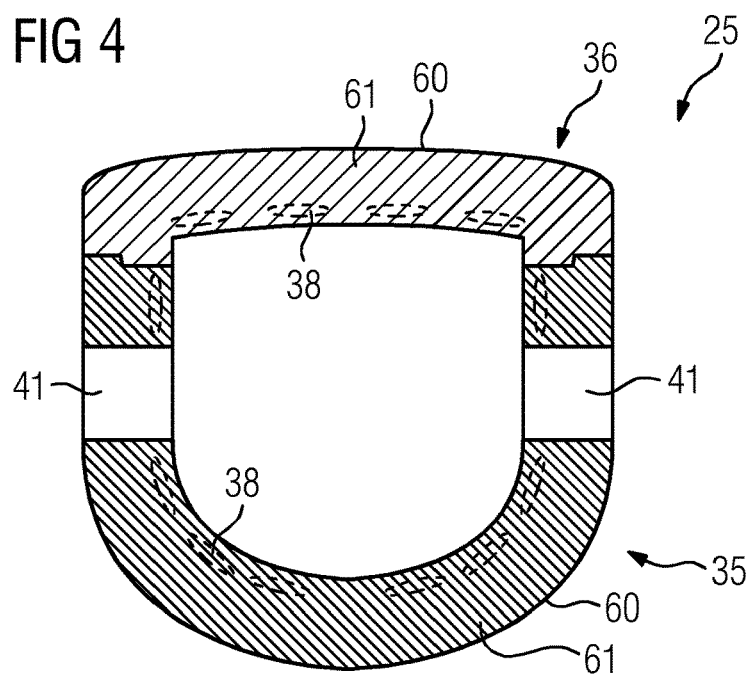
FIG. 4 depicts an alternative embodiment of the head coil as illustrated in FIG. 3.

FIG. 4 depicts an alternative embodiment of the head coil 25, which is similar in design to the embodiment shown in FIG. 3. Unlike that, however, here the housing interior 61, in which individual antennas 38, and also the further electronic components (likewise not shown in further detail) are accommodated, is designed such that it is filled with material. The housing 60 is formed here by a solid piece made of plastic, in which the electronic components are embedded. The individual antennas 38, and also the further electronic components, are incorporated into the housing 60 during the manufacture thereof (e.g., the electronic components are extrusion-coated with plastic). The housing 60 is manufactured, for example, from polypropylene. Alternatively, the housing 60 is not a solid piece made of plastic, but a piece made of plastics foam, which is optionally manufactured in a foam injection molding method or as particle foam. In this case, too, the electronic components are embedded into the foam body during the manufacture of the housing 60.

The embodiment shown in FIG. 5 corresponds to the embodiment according to FIG. 4, but here the head support 30, which according to FIG. 1 is shown as a separate component, is an integral part of the first local coil arrangement 35.

For this purpose, the head support 30 includes two base plates 80, which are each connected in one piece to the housing 60. The head support 30 further includes two fixing screws 81, which are adjustable with respect to the base plates 80. Additionally, the rear wall 45 of the housing 60 is configured to be flattened towards the outside, such that the local coil arrangement 35 may be positioned in a stable position on the patient couch 15.

For explanatory purposes, the base plates 80 are shown here as components that are separate from the housing 60, which are molded to fit precisely into the apertures 41 in the side walls 40. The base plates 80 are actually, however, monolithically connected to the housing 60, and are also manufactured accordingly during the manufacture of the housing 60. Accordingly, the base plates 80 are likewise manufactured from polypropylene. A continuous internal thread is created in each base plate 80, in which the fixing screw 81, which is provided in each case with a matching external thread 83, engages. According to the intended use thereof, the fixing screws 81 are used to fix the head 20 of the patient 5 in a specified position with regard to the head coil 25 with its respective screw foot 85. A screw head 86, which is provided to turn the fixing screw 81, is accessible here from outside the head coil 25.

Due to the integration of the head support 30 with the housing 60, a physician providing treatment has a particularly large free space in which to move around when carrying out the intervention, which simplifies the medical intervention. In particular, the physician providing treatment may use the free space for his hands or for medical instruments (needles, knives, a microscope, further theater instruments, etc.). Furthermore, the angle of access at which the medical instrument is guided to the head 20 (e.g., to the intervention site), is virtually freely selectable, as a result of which the intervention further becomes easier to carry out.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A local coil arrangement for use in an intervention supported by magnetic resonance imaging, the local coil arrangement comprising:
   a plurality of electronic components comprising at least one individual antenna configured to receive a magnetic resonance signal; and
   a housing that encloses a hollow or material-filled housing interior, wherein the plurality of electronic components is accommodated in the housing interior,
   wherein the housing interior is hermetically sealed, and
   wherein the housing is configured to be pressure- and temperature stable, such that the local coil arrangement is steam-sterilizable.

2. The local coil arrangement of claim 1, wherein the local coil arrangement is configured to transmit the magnetic resonance signal wirelessly to a readout unit of a magnetic resonance tomography (MRT) system.

3. The local coil arrangement of claim 2, wherein the wireless transmission is an inductive transmission.

4. The local coil arrangement of claim 3, wherein the housing is configured to be terminal-free.

5. The local coil arrangement of claim 2, wherein the housing is configured to be terminal-free.

6. The local coil arrangement of claim 1, further comprising:
   a support for a part of a body of an examination subject,
      wherein the support is permanently connected to the housing, and
   wherein the support is configured to be steam-sterilizable.

7. The local coil arrangement of claim 1, wherein the housing comprises at least two housing components assembled to provide the hollow housing interior along corresponding connecting edges of the two housing components.

8. The local coil arrangement of claim 7, wherein the corresponding connecting edges of the two housing components are provided with at least one seal or are joined together in a seamless connection.

9. The local coil arrangement of claim 8, wherein the corresponding connecting edges of the two housing components are glued or welded together.

10. The local coil arrangement of claim 1, wherein the housing comprises a plastic configured to hermetically seal the housing interior and enclose the plurality of electronic components in a molding.

11. The local coil arrangement of claim 10, wherein the housing comprises an injection molded plastic, a foam injection molded plastic, or a particle foam plastic.

12. The local coil arrangement of claim 1, further comprising:
   a moisture sensor, a temperature sensor, or both the moisture sensor and the temperature sensor arranged in the housing interior.

13. The local coil arrangement of claim 12, further comprising:
   a support for a part of a body of an examination subject,
      wherein the support is permanently connected to the housing, and
   wherein the support is configured to be steam-sterilizable.

14. The local coil arrangement of claim 1, wherein, in at least one section of the housing, the housing comprises a transparent material configured to provide for a visual inspection of the housing interior.

15. A magnetic resonance tomography (MRT) system to provide imaging support for an intervention with a local coil arrangement, the MRT system comprising:
   a local coil arrangement having:

a plurality of electronic components comprising at least one individual antenna configured to receive a magnetic resonance (MR) signal; and a housing that encloses a hollow or material-filled housing interior, wherein the plurality of electronic components is accommodated in the housing interior, wherein the housing interior is hermetically sealed, and wherein the housing is configured to be pressure- and temperature stable, such that the local coil arrangement is steam-sterilizable.

16. The MRT system of claim 15, further comprising:

a readout unit configured to wirelessly receive the MR signal transmitted by the local coil arrangement; and a computation unit connected by signal technology to the readout unit, wherein the computation unit is configured to evaluate the received MR signal.

17. The MRT system of claim 16, wherein the computation unit is further configured to detect a presence of the local coil arrangement based on a presence of a connector that is separate from the local coil arrangement on a specified port of the MRT system or based on a software-based user input.

* * * * *